(12) United States Patent
Fairbourn et al.

(10) Patent No.: US 9,913,947 B2
(45) Date of Patent: Mar. 13, 2018

(54) SILANE COATING FOR MEDICAL DEVICES AND ASSOCIATED METHODS

(75) Inventors: David C. Fairbourn, Sandy, UT (US); Edward A. Loeser, Sandy, UT (US)

(73) Assignee: Organic Cautery, LLC, Salt Lake City, UT (US)

( * ) Notice: Subject to any disclaimer, the term of this patent is extended or adjusted under 35 U.S.C. 154(b) by 1645 days.

(21) Appl. No.: 13/138,864

(22) PCT Filed: Apr. 9, 2010

(86) PCT No.: PCT/US2010/001069
§ 371 (c)(1),
(2), (4) Date: Oct. 11, 2011

(87) PCT Pub. No.: WO2010/117468
PCT Pub. Date: Oct. 14, 2010

(65) Prior Publication Data
US 2012/0029514 A1 Feb. 2, 2012

Related U.S. Application Data

(60) Provisional application No. 61/212,395, filed on Apr. 10, 2009.

(51) Int. Cl.
*A61B 18/14* (2006.01)
*A61M 5/32* (2006.01)
(Continued)

(52) U.S. Cl.
CPC ............ *A61M 5/329* (2013.01); *A61B 18/14* (2013.01); *A61L 31/022* (2013.01); *A61L 31/10* (2013.01); *C09D 183/06* (2013.01); *C09D 183/14* (2013.01); *C09D 183/16* (2013.01); *C25D 11/022* (2013.01); *C25D 11/26* (2013.01); *A61B 17/06066* (2013.01); *A61B 17/3211* (2013.01); *A61B 2017/00526* (2013.01);
(Continued)

(58) Field of Classification Search
CPC .. A61B 2018/1412; A61B 2018/00595; A61B 2018/00083; A61B 2018/0013
USPC .......................................................... 606/45
See application file for complete search history.

(56) References Cited

U.S. PATENT DOCUMENTS 3,488,265 A 1/1970 Morris
3,663,379 A 5/1972 Kendall
(Continued)

FOREIGN PATENT DOCUMENTS

EP 08153657.5 12/2008
WO 2010/117468 10/2010

OTHER PUBLICATIONS

Molitor, P., Barron, V., Young, T. Surface Treatment of Titanium for Adhesive Bonding to Polymer Composites: A Review (2001). Inter Jour Adhesion and Adhesives 21, 129-136.*
(Continued)

*Primary Examiner* — Jaymi Della
*Assistant Examiner* — Eunhwa Kim
(74) *Attorney, Agent, or Firm* — TraskBritt, P.C.

(57) ABSTRACT

A titanium electrosurgical instrument, such as a scalpel (20), and electrosurgical devices, e.g., needle (40), and Bovie tips (40), are provided with a silane coating (30) directly against the solid titanium metal (26, 43, 73) of the body tissue-contacting distal ends (24, 47, 70) thereof whereby to impart advantageous non-stick properties thereto.

17 Claims, 3 Drawing Sheets

(51) Int. Cl.
*A61L 31/02* (2006.01)
*A61L 31/10* (2006.01)
*C09D 183/06* (2006.01)
*C09D 183/14* (2006.01)
*C09D 183/16* (2006.01)
*C25D 11/26* (2006.01)
*C25D 11/02* (2006.01)
*A61B 17/06* (2006.01)
*A61B 17/3211* (2006.01)
*A61B 17/00* (2006.01)
*A61B 18/00* (2006.01)
*C08G 77/18* (2006.01)
*C08G 77/50* (2006.01)
*C08G 77/60* (2006.01)

(52) U.S. Cl.
CPC ............... *A61B 2017/00831* (2013.01); *A61B 2017/00849* (2013.01); *A61B 2018/0013* (2013.01); *A61B 2018/00107* (2013.01); *A61B 2018/00136* (2013.01); *C08G 77/18* (2013.01); *C08G 77/50* (2013.01); *C08G 77/60* (2013.01)

(56) References Cited

U.S. PATENT DOCUMENTS

| | | | |
|---|---|---|---|
| 3,840,442 A | | 10/1974 | Chevalier et al. |
| 3,959,091 A | | 5/1976 | Moji et al. |
| 4,674,498 A | | 6/1987 | Stasz |
| 4,677,147 A | | 6/1987 | Swihart et al. |
| 4,802,476 A | | 2/1989 | Noerenberg et al. |
| 4,922,903 A | | 5/1990 | Welch et al. |
| 4,927,420 A | | 5/1990 | Newkirk et al. |
| 5,030,218 A | * | 7/1991 | Alexander ............ 606/45 |
| 5,217,458 A | | 6/1993 | Parins |
| 5,342,381 A | | 8/1994 | Tidemand |
| 5,395,369 A | | 3/1995 | McBrayer et al. |
| 5,396,900 A | | 3/1995 | Slater et al. |
| 5,454,809 A | * | 10/1995 | Janssen ............ A61B 18/12 600/439 |
| 5,733,283 A | * | 3/1998 | Malis et al. ............ 606/48 |
| 5,924,206 A | * | 7/1999 | Cote et al. ............ 30/337 |
| 6,054,522 A | | 4/2000 | Carre et al. |
| 6,509,101 B2 | | 1/2003 | Fairbourn |
| 6,540,745 B1 | * | 4/2003 | Fairbourn et al. ............ 606/45 |
| 2003/0000847 A1 | | 1/2003 | Ostrovsky |
| 2005/0178664 A1 | | 8/2005 | Ostrovsky |
| 2007/0276458 A1 | | 11/2007 | Boser |
| 2010/0168745 A1 | | 7/2010 | Loeser |

OTHER PUBLICATIONS

Difference Between Steel and Titanium. 2010. Difference Between. Retrieved on Apr. 25, 2017 from http://www.differencebetween.net/object/difference-between-steel-and-titanium/.*
PCT International Search Report, PCT/US2010/001069, dated Jan. 31, 2011.
Xyanyong et al., Materials Science and Engineering R 47 (2004), pp. 49-121, see abstract, pp. 73-78.
Sul et al., The electrochemical oxide growth behaviour on titanium in acid and alkaline electrolytes, Medical Engineering & Physics, 2001, pp. 329-46, vol. 23.
What is the difference between the different grits of sandpaper?—HowStuffWorks, accessed Mar. 31, 2015, at http://home.howstuffworks.com/difference-between-grits-sandpaper.htm/printable.
Roughened—definition of roughened by The Free Dictionary, accessed Apr. 3, 2015, at http://www.thefreedictionary.com/roughened.
Roughen—definition of roughen by The Free Dictionary, accessed Apr. 3, 2015, at http://www.thefreedictionary.com/roughen.

* cited by examiner

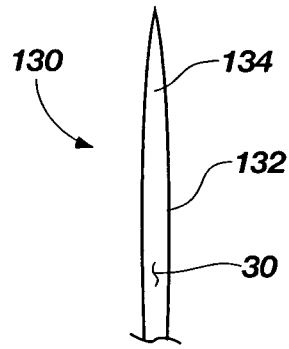
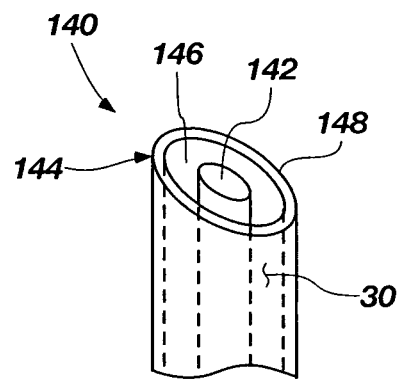
FIG. 8  FIG. 9
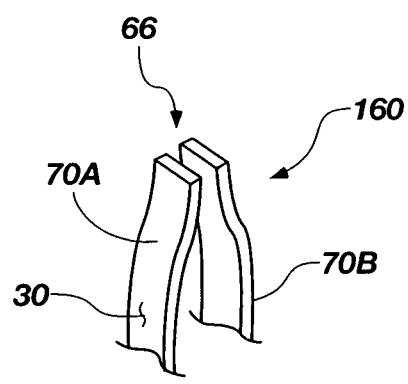
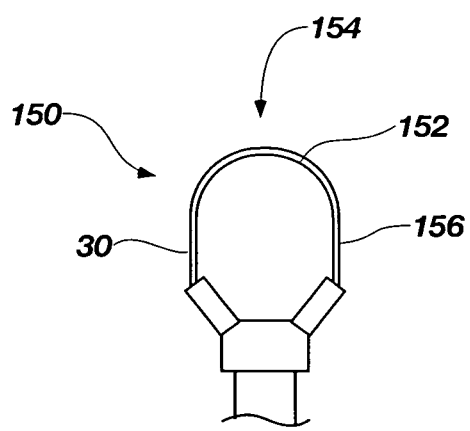
FIG. 10  FIG. 11

SILANE COATING FOR MEDICAL DEVICES AND ASSOCIATED METHODS

PRIORITY CLAIM

This application claims the benefit of the filing date of U.S. Provisional Patent Application Ser. No. 61/212,395, filed on Apr. 10, 2009, for "Silane Coating for Medical Devices and Associated Methods."

TECHNICAL FIELD

The invention relates generally to medical devices and associated methods. More specifically, the invention relates to medical devices with an advantageous coating.

BACKGROUND

Medical devices are used to treat human or animal tissue in many ways. Many such devices are elongated with one end adapted to be held, either by hand or by a robotic or other mounting, with the other end being comprised of a parent metal and adapted to contact or otherwise interact with human or animal tissue.

By way of an example, a needle has a proximal end adapted to be mounted to a syringe cannula for injection or withdrawal of fluids from a body, or to a length of flexible tubing such as in an IV catheter. In either case, the metal distal end is adapted to be inserted into and through human or animal skin and blood vessels for passage of fluids therethrough.

One specialized type of medical instrument is an electrosurgical knife or RF scalpel which is used to cut or cauterize tissue. Typical of such instruments is that they use an elongated medical device referred to as an "active electrode," or tip, sometimes also referred to as a "Bovie" tip, to contact and cauterize the tissue.

In electrosurgery, an electric current is used to cut or cauterize human or animal tissue. Currently, there are two main types of electrosurgical apparatus in use. Depending on the number of electrodes used in the cutting and cauterization, these instruments are referred to as, unipolar or bipolar. The tip is electrically conductive and cooperates with another conductor, such as a dispersive electrode (monopolar or unipolar) or an adjacent electrode or tip (bipolar), to allow current flow at the site to be treated. These tips have a proximal end adapted to be mounted to the knife, with the distal end defining an active metal electrode area to cut or cauterize tissue of interest.

In a unipolar electrosurgical apparatus, current (usually "RF" current) is supplied to an electrode which is used to cut or cauterize tissue. When in use, current flows through the electrode to the patient and the circuit is completed using a "patient plate" on which the patient lies. The surface area of the electrode through which current flows (the "active electrode area" or "active electrode surface") is small relative to the area of the patient plate and therefore an intense local current density is generated at the electrode. This results in cutting or cauterization of the tissue in the immediate proximity of the electrode. An example of a unipolar electrosurgical instrument is described in U.S. Pat. No. 4,927,420.

In a bipolar electrosurgical apparatus, the "patient plate" of the unipolar apparatus is replaced by a second electrode separated from the first electrode by a small gap. In operation, an intense local current density is generated between the electrodes and results in cutting or cauterization of the tissue between the electrodes. Examples of bipolar electrosurgical instruments are described in U.S. Pat. Nos. 5,396,900, 5,217,458, 5,342,381, and 5,395,369.

The electrodes used in both unipolar and bipolar apparatus come in a wide variety of shapes, sizes, and configurations. Depending on the surgical requirements, the electrodes can be in any of a variety of shapes, non-limiting examples include needles, loops, spatulas, scalpel blades, scissors, forceps, and balls. Electrosurgical techniques have also been extensively used for endoscopic surgery. Since electrosurgical tools can be made much smaller than their conventional counterparts, electrosurgery is especially suited to this type of surgery. A wide variety of shapes and configurations of endoscopic electrodes have been described as seen in the herein cited U.S. Pat. Nos. 5,396,900, 5,217,458, and 5,395,369.

In conventional electrosurgical instruments, the active electrode surfaces are usually made of stainless steel. However, there is a well known drawback to using stainless steel electrodes; namely, that burnt tissue layers adhere to the electrode surface during the electrosurgical procedure. This drawback is especially disadvantageous during endoscopic surgery as the cleaning of the electrosurgical tip is an arduous task, adding considerable time and expense to each procedure.

It is thought that the mechanism that causes tissue to stick to the instruments is as follows. During electrosurgical procedures, an intense electric current density is generated between the electrodes and the tissue. In fact, the electrosurgical procedure often causes arcing between the electrode and the tissue. The high current density causes intense heating which carburizes the tissue and results in the required cutting or cauterization. The electrodes of the conventional instruments react with this carburizing atmosphere and this forms adherent burnt tissue layers on the surface of the electrodes. During the electrosurgical procedure, burnt tissue begins to build up on the instrument surfaces in the form of a black film. When this build-up thickens and thus reduces the current density between the electrode and the tissue, the tissue begins to stick to the hot black film. The surgeon is then forced to stop the operation and clean the electrosurgical instrument. This cleaning, in addition to being time consuming, can require enough force to scratch the surface of the stainless steel. These scratches roughen the surfaces of the instrument and this in turn causes tissue residue to build up faster and results in more sticking.

The metal electrodes of electrosurgical instruments have been coated with organic materials, such as polytetrafluoroethylene ("PTFE") also known as TEFLON® or other polymers. Unfortunately, these low melting, volatile materials cannot withstand the high localized temperatures of the electric discharge between the electrode surface and the tissue. The resulting products of these melted, and at times, vaporized, coatings, are known to form harmful chemicals and undesirable products which deposit into the wound in the tissue being cut and cauterized. Surgical staffs have reported that after exposure to these vaporized organic coatings, flu-like symptoms result. This problem has been termed "polymer fume fever" or "TEFLON flu." PTFE material is not always easy to apply and is not a good conductor. A further disadvantage is that a coating of organic material is melted in the very early stages of the electric discharge and therefore provides little or no improvement in the reduction of tissue adhesion. It is typical for the surface of a conventional stainless steel electrode to be roughened prior to conventional coating with PTFE material to improve the mechanical bond between the stainless steel and the coating. When the coating melts and reveals the roughened metal surface, this promotes increased pitting of the metal surface. This pitting can result in transfer of the metal from the electrode to the tissue. In addition the roughened metal surface can also exacerbate the problem of tissue buildup as discussed above.

Applying a layer of PTFE or TEFLON®, has another significant drawback, it has a tendency to scratch or abrade thereby diminishing the non-stick performance of the medical instrument. The non-stick properties of PTFE once diminished or lost, such as from being scratched or abraded, may not be readily repaired.

Another non-stick coating is discussed in U.S. Pat. No. 4,677,147. The coating involves the reaction of four components, i.e., thermostable polyorganosiloxane resin, a non-thermostable polyorganosiloxane resin, and two different metal salts of carbosylicacids. The need to use two different varieties of siloxane, and the metals, introduces cost and complexity. Silane coatings for glassware is described in U.S. Pat. No. 6,054,522.

Other examples are to plate the tip of the electrosurgical instrument with platinum or coat the tip with conductive ceramic. The plating or coating process can be quite complex and costly. Platinum is very costly, and ceramics can be quite brittle, the exposing the patient to risk of injury if pieces of ceramic chip or break off from the tip.

Another proposed solution to the problem of tissue adhesion is the use of a vibrating blade. (See, e.g., U.S. Pat. Nos. 4,674,498, 4,802,476, and 4,922,903.) These references describe electrosurgical apparatus including means for vibrating an electrosurgical blade during use to prevent buildup of tissue and debris on the blade. This technique requires the apparatus to include a means for vibrating and a means for coupling the vibrations to the electrosurgical instrument. This increases the cost and complexity of the apparatus and in some cases, for instance endoscopic surgery, may present great technological problems.

The issue of tissue buildup on electrosurgical instruments during electrosurgical procedures is a problem with these techniques that has yet to find an adequate solution. Although some solutions to this problem have been proposed, each has their own drawbacks. There is a long felt need for electrosurgical instruments to which tissue does not adhere, and which can be formed in a wide variety of shapes. It would be an improvement in the art to replace the current non-stick coatings with other anti-adhesion materials.

DISCLOSURE OF THE INVENTION

The invention provides a low cost, reliable non-stick coating for the metal, body tissue-contacting distal end of medical devices, and in the case of electrosurgical knife tips also affords desired conductivity, without the drawbacks associated with other solutions to the problem of tissue adherence and buildup. The invention relates to utilization of silane coating. More specifically, the invention relates to using silane coating on roughened, anodized titanium electrosurgical instruments in order to provide desirable properties, characteristics and/or attributes to the surface.

Implementation of the invention takes place in association with a surface, such as at least a portion of the surface of an electrosurgical tip that may be used to cut tissue and/or cauterize blood vessels and/or tissue of a patient during a surgical operation. In accordance with the principles of the invention, a medical device has a proximal end portion adapted to be held and distal end portion comprised of a parent metal and which is adapted to contact and/or interact with tissue, with at least a selected portion or aspect or all of the distal end portion, such as the active electrode area of an electrosurgical knife tip, provided with a coating consisting essentially of a silane directly applied to the parent metal at the surface of the distal end. Preferably, the parent metal is titanium. The titanium could be pure titanium metal or titanium alloys. There are numerous alternative methods of machining the Bovie tips from rod formed titanium. The titanium is then anodized, see, e.g., U.S. Pat. Nos. 3,840,442, 3,663,379, 3,959,091, and 3,488,265.

Anodizing the titanium medical instruments creates a coating similar to aluminum anodizing. Anodizing works on aluminum, and not on stainless steel, because the anodizing process results in pores 30 angstroms across. This provides an advantage over the process applied to stainless steel as the slipperiness fades after 8-10 uses. The anodizing of the titanium medical instruments advantageously prepares the surface for the silane solution coating. Particularly, we observed that producing an oxidized surface produced a slick surface with titanium, not seen with oxidizing aluminum or steel in a like manner.

Silane coating has been used to provide a non-stick surface on cooking utensils as described in U.S. Pat. No. 6,509,101. The non-stick coatings with silane for cooking utensils in U.S. Pat. No. 6,509,101 provides a simpler technique than a multi-siloxane and metal reaction coating as discussed above. In addition, this coating provides better non-stick properties than a hard anodized surface, as well as offering a non-stick surface which may be readily repaired if scratched or abraded. To this end, and in accordance with the principles of the present invention, the surface of the electrosurgical device is coated with an aqueous/alcohol silane solution which is then heated to form a semi-permanent, in situ polymerized, coating thereon. The resulting coating is thus easily applied to afford advantageous non-stick properties.

The silane solution may advantageously be comprised of components which, when heated, will form the coating. As a consequence, if the silane coating becomes scratched or abraded, it may be refurbished or renewed simply by applying an additional amount of the silane solution and heating same. Such a procedure may be carried out by the consumer or the hospital staff, who may be provided with a quantity of the silane solution. The silane reacts with the metal surface to form the non-stick coating. The silane is a trialkoxyalkane silane. One such solution includes only Bis(triethoxysilyl)etane (BTSE) or Bis(trimethoxylsilyl)methane (BTSM).

Described herein are processes for producing an anodized solid titanium non-stick electrosurgical device, having a proximal end adapted to be held and a distal end with an active electrode area, the distal end adapted to contact body tissue. Such a process comprises roughening and anodizing the solid titanium electrosurgical device, coating the same with a liquid silane solution directly against the anodized solid titanium electrosurgical device of at least a selected portion of the active electrode, and polymerizing the silane coating so as to produce an anodized solid titanium non-stick electrosurgical device.

Also described herein are anodized solid titanium non-stick electrosurgical devices with a proximal end adapted to be held and distal end with an active electrode area comprised of solid titanium and adapted to contact body tissue, with the solid titanium electrosurgical device is anodized and coated with in situ polymerized silane coating directly against the solid titanium of at least a selected portion of the active electrode area. The polymerized silane coating of the active electrode area of the solid titanium electrosurgical device is non-stick as may be determined by reduction in carbonaceous remains sticking to the active electrode area while the electrosurgical device is used in an electrosurgical procedure.

Further described herein are methods of utilizing an anodized solid titanium non-stick electrosurgical device with a proximal end adapted to be held and distal end with an active electrode area comprised of solid titanium and adapted to contact body tissue, with the solid titanium electrosurgical device is anodized and coated with silane coating directly against the solid titanium of at least a selected portion of the active electrode area. The silane coated anodized solid titanium electrosurgical device is heated to a temperature adequate to in situ polymerize the silane coating, with the coating is non-stick as may be determined by reduction in carbonaceous remains sticking to the active electrode area while the electrosurgical device is used in an electrosurgical procedure. The electrosurgical device conducts energy to the body tissue during an electrosurgical procedure, through the active electrode area of the anodized solid titanium electrosurgical device.

By virtue of the foregoing, there is thus provided improved coatings for medical instruments which is simpler than a multi-siloxane and metal reaction coating, imparts advantageous non-stick properties to the medical instrument, and which may be easily repaired if scratched or abraded.

BRIEF DESCRIPTION OF THE DRAWINGS

FIG. 8 is a third alternative active electrode area of a Bovie tip with a silane coating.

FIG. 9 is a fourth alternative active electrode area of a Bovie tip with a silane coating.

FIG. 10 is a fifth alternative active electrode area of a Bovie tip with a silane coating.

FIG. 11 is a sixth alternative active electrode area of a Bovie tip with a silane coating.

MODE(S) FOR CARRYING OUT THE INVENTION

Figure 1:
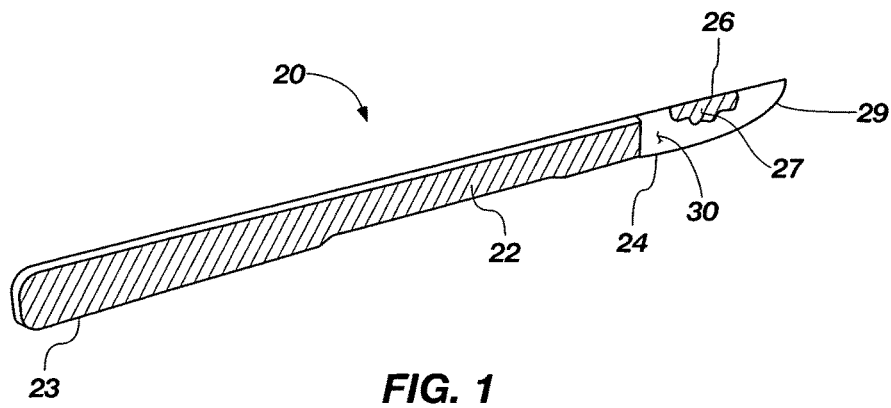
FIG. 1 is a perspective, partially cut-away view of a first exemplary medical device in the form of a scalpel with a silane coating.

With reference to FIG. 1, there is shown in perspective view a medical device 20 such as a scalpel being an elongated metal member 22 having a proximal handle end 23 adapted to be held such as by a surgeon's hand (not shown) and a distal integral or detachable cutting end 24 adapted to contact and/or interact with tissue (not shown). Cutting end 24 of scalpel 20 is typically comprised of a primary or parent metal 26 such as an alloy or composite, to thus have at the surface(s) 27 thereof the parent metal 26 making up distal end 24. Distal end 24 is desirably able to glide along human tissue (not shown) as the knife edge 29 thereof cuts same and without unduly sticking thereto. To this end, and in accordance with the disclosure herein, some selected portion or aspect or all of cutting end 24 is provided with a silane coating 30 which is associated with (e.g., applied directly to or otherwise against) parent metal 26 at surface(s) 27 making up cutting end (not shown) and without an intervening carrier layer, such as a sintered frit for example, by which to support coating 30.

The parent metal 26 is titanium or titanium alloy. The titanium may be commercially pure (CP) titanium, which is alpha in structure. "Pure" titanium usually has some amount of oxygen alloyed within it. CP titanium is the weakest, but most corrosion-resistant type of titanium. The content of interstitial oxygen and nitrogen increase the strength of CP titanium. The primary difference between CP grades is oxygen and iron content, with tensile property being primarily affected by the oxygen content. The titanium alloy may be Ti-8Al-1Mo-1V (Ti-811), the Unified Numbering System (UNS) Number R54810, which is a metallurgical alpha-beta alloy, containing the alpha stabilizer, aluminum (Al), and a small amount of the beta stabilizer, molybdenum (Mo) and vanadium (V) (plus iron as an impurity). The titanium alloy may alternatively be Ti-6Al-2Sn-4Zr-2Mo (Ti-6242), UNS Number R54620, which is a metallurgical alpha-beta alloy. The tin (Sn) and zirconium (Zr) additions are solid-solution strengthening elements which are neutral phase stabilizers. The 2 percent molybdenum addition is a beta-phase stabilizer; the aluminum is the alpha-phase stabilizer. This alloy is considered to be weakly beta stabilized, and is thus described as a near-alpha, alpha-beta alloy.

Prior to coating, the surface(s) 27 of cutting end 24 are first advantageously polished to a rough surface using, e.g., a sand blaster, and then, after wiping clean, cutting end 24 is immersed in a solution containing 10% by volume of hydrogen peroxide (30% commercial concentration), (not shown) until a water break can be seen. Cutting end 24 then undergoes a process in reverse to electroplating. A voltage of between 3 and 6 volts is applied with the anode being the titanium Bovie tip and the cathode being a piece of graphite. Optionally the cathode can be stainless steel or nobium clad with platinum. The methods for anodizing can be found in the herein cited U.S. Pat. Nos. 3,840,442, 3,488,265, 3,663,379, and 3,959,091. A liquid solution of silane 30 is then applied, such as by spraying, dipping or painting, to the surface(s) 27 of cutting end 24, or those portions thereof desired to be coated. The liquid silane is then dried to form the hard coating 30. While one or more layers of coating 30 may be applied, it will be appreciated that the resultant coating applied to surfaces(s) 27 consists essentially of the silane (in one or more layers) without either a precursor or a subsequent coating of a different material (all not shown). Further advantageously, silane coating 30 is formed by applying an uncross-linked or monomeric liquid silane to surface(s) 27 which liquid silane is then polymerized in situ. The silane in its liquid state may further be halogen-free and/or a polyfunctional silane.

Figure 2:
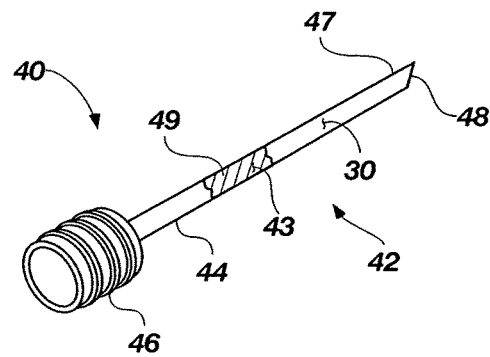
FIG. 2 is a perspective, partially cut-away view of a second exemplary medical device in the form of a needle with a silane coating.

With reference to FIG. 2, there is shown a second exemplary medical device 40, a needle (shown enlarged). Needle 40 is an elongated member 42 comprised of a parent metal 43 at surface 49. Member 42 has a proximal end 44 adapted to be held such as by a syringe mount 46 or a catheter tube mount (not shown). The distal end 47 of needle 40 is sharpened as at 48 so as to puncture tissue (not shown) such as the skin and/or a blood vessel wall. To facilitate ease of entry thereof into the tissue (not shown) and/or through a sheath introducer or the like (not shown), at least a selected portion or aspect of the surface 49 of needle 40 at distal end 47, such as tip 48, if not all of needle 40, is roughened and coated with silane 30 directly against the parent metal of needle 40 as above described in the case of distal end 24 of scalpel 20.

Figure 3:
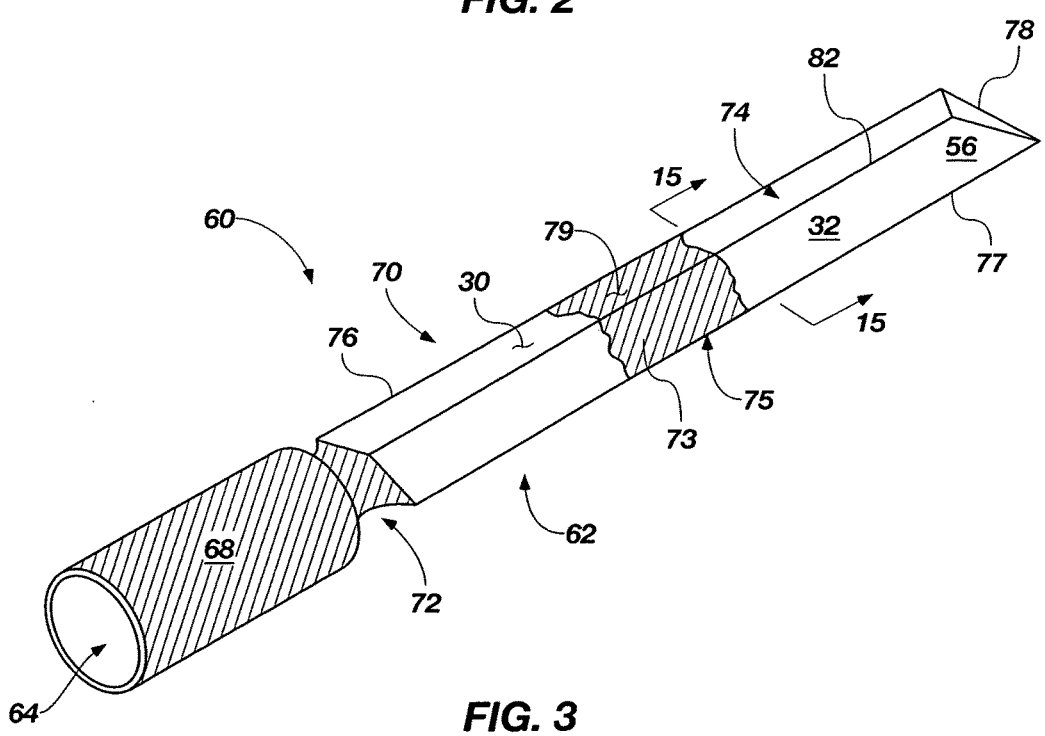
FIG. 3 is a perspective, partially cut-away view of a third exemplary medical device in the form of a first Bovie tip with a silane coating.
Figure 5:
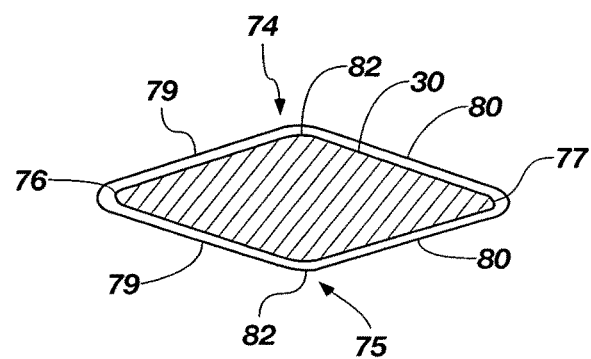
FIG. 5 is a view taken along lines 15-15 of FIG. 3.
Figure 6:
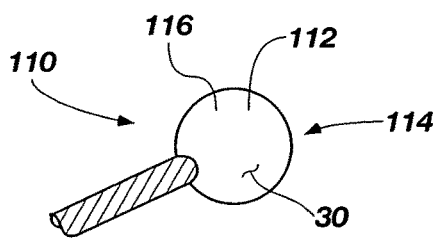
FIG. 6 is a first alternative active electrode area of a Bovie tip with a silane coating.
Figure 7:
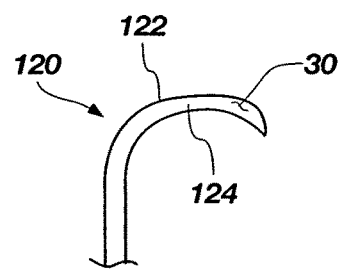
FIG. 7 is a second alternative active electrode area of a Bovie tip with a silane coating.

With reference to FIG. 3, shown in perspective view is a third exemplary medical device 60, a first electrosurgical knife tip in the form of a Bovie tip. As characteristic of many medical devices, tip 60 is an elongated titanium metal 62 extending between a proximal end 64, and a distal end 66. Member 62 includes a shaft 68 extending from proximal end 64, such as a cylindrically shaped shaft adapted to be held, manipulated or mounted, e.g., by being coupled to an electrosurgical knife handle (not shown). Extending from distal end 66 of member 62 is a portion 70, such as an active electrode area, which is adapted to contact body tissue (not shown), e.g., for cutting and/or cauterizing same. Shaft 68 and electrode area 70 are an integral unit and so may be seen to join together as at 72. Member 62 shown here is comprised of conductive parent metal 73, e.g., titanium or titanium alloy as described supra, such that shaft 68 and electrode area 70 are electrically conductive. For Bovie tips, electrode area 70 is generally characterized in that it is flattened as compared with shaft 68 so as to have an upper generally flat surface 74 and a lower generally flat surface 75 which surfaces meet at lateral edges 76, 77. Lateral edges 76, 77 may join along a front edge 78 at the distal end 66 of member 62. The flat surfaces 74 and 75 may be co-planar as in the case of a rectangular cross-section of area 70 (see FIG. 10) or may include canted flat walls 79, 80 extending from edges 76, 77, respectively, and joining along peak edges 82 to provide a diamond-shaped cross-section (FIG. 5). Either way, surfaces 74, 75 are considered generally flat in relation to the cylindrical shaft 68. Peak edges 82 of surfaces 74, 75 merge into front edge 78. Other shapes may be employed depending upon the characteristics of the medical device to be used, examples of which will be described with reference to FIGS. 6 through 10.

It is desired, that portion 70 be able to glide along body tissue (e.g., layers of fascia) without unduly sticking thereto. Moreover, where the device is an electrosurgical knife tip, it is desired that the area 70 move along the tissue without buildup of tissue or carbonaceous remains caused by cauterized tissue, yet also be able to conduct electricity generally uniformly across electrode area 70 in order to properly cauterize the tissue. To this end, some selected aspect or all of at least the distal portion 70, such as a portion of the electrode area of knife tip 60, is provided with a silane coating 30 (FIG. 5) applied directly to parent metal 73 of tip 60 such as at surface 74 and/or 75 and related edges 76, 77, 78 and/or 82.

Figure 4:
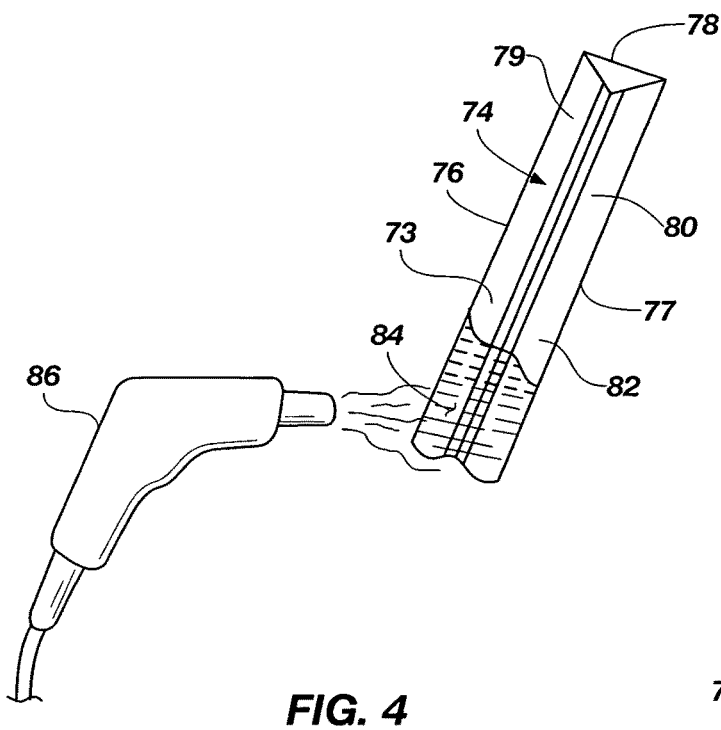
FIG. 4 is an enlarged, partially exposed view of the active electrode area of the Bovie tip of FIG. 3 showing application of liquid silane thereto.

Prior to coating, the surfaces and edges of electrode area 70 are roughened and coated with silane 30 directly against the titanium metal of electrode area 70 as described in the case of distal end 24 of scalpel 20. With reference to FIG. 4, a solution of monomeric or uncross-linked silane 84 is applied to the surface(s) and/or edge(s) of those portions of distal portion 70 which are desired to be coated. The silane solution 84 is applied in its liquid state or solution form directly to extend over flat surface 74 and/or flat surface 75, for example, so as to be directly against titanium metal 73. Advantageously, solution 84 is also applied to peak edge 82 and/or lateral edges 76 and 77, as well as front edge 78. Solution 84 may be readily applied in liquid form such as by spraying, dipping or painting thereon, by way of example.

The silane solution 84 includes only monomeric or uncross-linked silane and so is not a polymer as applied to the medical device. Advantageously, silane solution 84 does not include a halogen or metal and may be a polyfunctional silane. The solution 84 is then dried such as with a heat gun 86 to in situ polymerize the solution to form the hard coating 30 (FIG. 5). Liquid solution 84 may be the solution used to form coating 30 on the metal, tissue-contacting, distal ends 24 and 47 of devices 40 and 60 as well. A further layer of coating 30 may be applied if desired although it will be appreciated that the result is, in effect, that the coating applied to distal portion 70 consists essentially of silane without either a precursor or a subsequent coating of different material.

The result of coating is that the coated surfaces and edges are provided with a reliable, desirably slippery, non-brittle, non-stick silane coating that is also conductive so as to provide the advantages of TEFLON® coating, ceramic coating, platinum plating, and sintered frit, but without the drawbacks thereof. Additionally, the silane solution may be comprised of materials that form the coating at temperatures readily obtainable without expensive or complicated equipment.

The silane suitable for use in the present invention may have mono, bis, or tri functional trialkoxy silane, although polyfunctional silanes are preferred. The silane may be a bifunctional trialkoxy silyl, preferably trimethoxy or triethoxy silyl groups. Bisfunctional silane compounds are well known and two preferred for use in the present invention are bis(triethoxysilyl)ethane and bis(trimethoxysilyl)methane. In both of these compounds the bridging group between the two silane moieties is an alkyl group.

Additional commercially available poly functional silanes include: 1,2 bis(triethoxysilyl)ethane, 1,2 bis(trimethoxysilyl)methane, 1,2-Bis(tetramethyldisoloxanyl)Ethane, 1,9-Bis(triethoxysilyl), Bis(triethoxysilyl)Octane, Bis(trimethoxysilyl)Ethane, 1,3-Bis(trimethylsiloxy)-1,3-Dimethyl Disiloxane, Bis(trimethylsiloxy)Ethylsilane, and Bis(trimethylsiloxy)Methylsilane.

The silane is typically applied as an aqueous/alcohol solvent solution. The solvent solution will contain from about 1-2% to about 30% de-ionized water with the remainder being a lower alcohol such as methanol, ethanol, propanol or the like. Ethanol and methanol are preferred. The solvent is combined with the silane and generally acetic acids to establish a pH of about 4-6. The concentration of the silane compound is not relevant as long as the silane remains in solution during application. Generally, the solution will have about 1% to about 20% silane by weight.

One silane solution may be formed of a monomeric variety of silane such as an organofunctional silane such as BTSE 1,2 bis(triethoxysilyl)ethane or BTSM 1,2 bis(trimethoxysilyl) methane. The silane may be dissolved in a mixture of water and acetic acid at a pH of 4, thin in a denatured alcohol to establish the silane solution. The solution has about 10 ml of distilled, de-ionized, RO water, 190 ml of denatured alcohol (mixture of ethanol and isopropanol, N.O.S.) and glacial acetic acid with approximately 10 ml of the BTSE obtained from Aldridge Chemical. Silane concentration is between about 1% and 10% and advantageously about 5%. This readily forms the more or less permanent coating 30 at temperatures readily achieved.

The silane solution 84 is applied liberally and any excess is poured off. The scalpel end 24, needle end 47 and/or knife tip 60 and solution 84 thereon are then heated such as with a heat gun 86 (FIG. 4), or even in a conventional oven (not shown), or other heat source as may be used for sterilization of medical instruments, to about 400° F. for about 30 minutes, to in situ polymerize same and form coating 30. Prior to heating, the solution may first be allowed to dry thereon such as underneath a lamp (not shown). Heating of the solution to form coating 30 may be accomplished by heat treating scalpel 20, needle 40, or knife tip 60 with the silane solution 84 thereon. Generally, formed coating 30 will be 0.01 to 2.0 g/cm$^2$ of surface. In use (FIG. 4), solution 84 is applied directly to the parent metal at the roughened surface of those portions or all of the distal portion 24, 47 or electrode area 70 desired to be coated (and the proximal ends 24, 44 or shaft 68, if desired), and then heated to form a hard polyorganosilane coating 30. Scalpel 20 or needle 40 with silane coating 30 thereon, is then able to be used to contact and/or interact with tissue (not shown), and tip 60 with coating 30 thereon is then able to be used for electrosurgical procedures as desired by the surgeon (not shown), for example, all without any precursor such as sintered frit, or any further application of different coatings over silane coating 30.

As mentioned, the distal ends of medical devices may take many shapes, as exemplified by the various active electrode Bovie tips shown in FIGS. 6 through 11. To this end, a Bovie tip 110 (FIG. 6) may include a ball nose active electrode 112 at its distal end 114 and to be coated over its polished or roughened surface 116 with silane 30 in accordance with the principles of the present invention; Bovie tip 120 (FIG. 7) may include a hook end active electrode 122 coated with silane 30 on its smooth surface 124 in accordance with the principles of the present invention; Bovie tip 130 (FIG. 8) may include a needle-shaped active electrode 132 coated with silane 30 over its smooth surface 134 in accordance with the principles of the present invention; bipolar Bovie tip 140 (FIG. 9) is in the shape of a fine needle (shown greatly enlarged and not to scale) such as for eye surgery and may include an inner metal conductor, wire or tube rod, 142 extending to its distal end 144 with a surrounding plastic insulator ring or sheath 146 insulatively spacing an outer metal shell 148 therefrom, with shell 148 and/or distal end 144 of conductor 142 smoothed and coated with silane 30 in accordance with the principles of the present invention; and bipolar Bovie tip 160 (FIG. 10) may include two blade-like or rectangular in cross-section active electrodes 70A, 70B at the distal end 166, each of which is coated with silane 30 in accordance with the principles of the present invention. Bovie tip 150 (FIG. 11) may include a loop-like configuration active electrode 152 at its distal end 154 and to be coated over its polished or roughened surface 156 with silane 30 in accordance with the principles of the present invention.

By virtue of the foregoing, there is thus provided a low cost, reliable non-stick coating for the metal, tissue-contacting distal end of medical devices, and in the case of electrosurgical devices the coating also affords desired conductivity, without the drawbacks associated with platinum plating, TEFLON® coating, ceramic coating, or sintered frit precursor.

The following definitions are provided:

Electrosurgical device—any surgical instrument that is used for supplying electrical current to a subject. The subject may be either animal or human. Examples of electrosurgical instruments include, but are not limited to, Bovie Blades, bipolar forceps, cauterizing end effectors (for endoscopic surgery), bipolar biopsy devices, spatula blades, ball electrodes, arthroscopic hook electrodes, L and J hook electrodes (for laparoscopic surgery), extended blade electrodes, needle electrodes, extended needle electrodes, curved electrodes, angled blade electrodes, and loop electrodes (for histological examinations and gynecologic tissue extractions).

Active electrode area—that area of an electrosurgical instrument through which electric current is supplied to the subject.

Electrosurgical procedure—Also known as electrocautery is any procedure performed on body tissue that involves high-frequency alternating current delivered in either a unipolar or a bipolar fashion through an electrosurgical device. The effectiveness of the conversion of energy into heat is inversely related to the area of contact. As such the active electrosurgical area is preferably designed to be small to generate heat efficiently, and the returning electrode is preferably large to disperse energy and prevent any burn injury on the patient.

Anodizing—Also known as the anodizing process involves suspending the article to be anodized in an electrolyte which normally consists of an aqueous solution of acids, salts, or bases. A cathode o any suitable conductive material is also suspended in the solution so that when an external electric current source is used an oxidizing reaction is promoted between the anode, the article to be anodized, and the electrolyte to form an oxide type coating.

Polymerizing—This is a process of reacting monomer molecules together in a chemical reaction to form three dimensional networks also known as polymer chains.

In situ polymerizing—This is the process of polymerizing performed directly on the electrosurgical device such that the polymerized coating is bound to the electrosurgical device.

Silane—This is a chemical compound with the formula $SiH_4$, and can be thought of as the silicon analogue of methane $CH_4$.

While the silane coating in each case is monomeric or uncross-linked as applied, and then in situ polymerized, the coating could be applied in multiple layers of the same silane material. Also, while the silane coating as applied in its liquid form 84 advantageously has four attributes, i.e., it is polyfunctional silane, it is not a polymer, and it has no halogen or metal, and while the final coating has a fifth attribute, i.e., it is essentially the only coating, the coating could meet fewer than all five of the attributes, as long as in any given case at least one or more of them is met. Thus, by way of example, the liquid silane could be a monofunctional silane and/or have a halogen, provided the resultant coating is essentially the only coating on the device distal end. Alternatively, and by way of further example, a halogen-free, polyfunctional silane could be applied as one of many coatings. In addition to the foregoing, while the coating consists essentially of a silane, there could be included in the coating as applied silane and another materials which are either non-functional or may be necessary for medical applications, and the coating would still be considered to consist essentially of a silane. Further, while a scalpel, needle and Bovie tip are described, other medical devices having different geometric shapes than that shown herein, with a proximal end adapted to be held and a metal distal end adapted to contact and/or interact with tissue (not shown) (which may be skin, bodily fluid and/or solid masses), may be coated with silane 30 to obtain the advantages of the present invention. Further, other knife tip configurations may be utilized having active electrode areas of different shapes, such as blade-like, ball or spherical, paddle, hook, round loops, needles, and/or canonization electrodes, which shapes may be advantageously coated with silane 30 to provide the advantages of the invention.

REFERENCE

Donachie, Matthew J., "Titanium: A Technical Guide." ASM International, 2000.

What is claimed is:

1. A process of producing an anodized solid titanium non-stick electrosurgical device, the process comprising:
    a) providing a solid titanium electrosurgical device, having a proximal end adapted to be held and a distal end with an active electrode area; wherein the distal end is adapted to contact body tissue;
    b) roughening a selected portion of the active electrode area of the distal end;
    c) immersing the selected portion of the active electrode area in hydrogen peroxide and then anodizing the solid titanium electrosurgical device with an anode and a cathode by applying a voltage with the anode being the selected portion of the active electrode area and the cathode made of a material selected from the group consisting of niobium clad with platinum, graphite, and stainless steel;
    d) applying silane directly against the anodized solid titanium electrosurgical device of at least a selected portion of the roughened active electrode area to form a silane coating; and
    e) polymerizing the silane coating so as to produce an anodized solid titanium non-stick electrosurgical device.

2. The process of claim 1, further comprising:
    after the silane coating has become scratched or abraded, reapplying silane coating in a liquid state over the anodized and scratched and/or abraded anodized solid titanium electrosurgical device;
    re-polymerizing the silane coating,
    re-sterilizing the anodized solid titanium electrosurgical device for re-use.

3. The process of claim 1, wherein roughening the selected portion of the active electrode area comprises sand blasting the active electrode area.

4. The process of claim 1, wherein the silane coating comprises a bifunctional silane compound.

5. An anodized solid titanium non-stick electrosurgical device, comprising:
    a proximal end adapted to be held, and
    a distal end with an active electrode area comprised of solid titanium and adapted to contact body tissue,
    wherein at least a portion of the active electrode area of the distal end has been roughened, anodized, and coated with in situ polymerized silane coating so that the silane is coated directly against the anodized solid titanium; and
    wherein the in situ polymerized silane coating of the active electrode area of the anodized solid titanium non-stick electrosurgical device is non-stick as may be determined by reduction in carbonaceous remains sticking to the active electrode area while the anodized solid titanium non-sick electrosurgical device is used in an electrosurgical procedure.

6. The anodized solid titanium non-stick electrosurgical device of claim 5, wherein the in situ polymerized silane coating comprises a:
    bifunctional silane compound selected from the group consisting of, 1,2 bis(triethoxysilyl) ethane, 1,2 bis (trimethoxysilyl) methane, 1,2-Bis(tetramethyldisoloxanyl) Ethane, 1,9-Bis(triethoxysilyl) Nonane, Bis (triethoxysilyl) Octane, Bis(trimethoxysilyl) Ethane, 1,3-Bis(trimethylsiloxy)-1,3-Dimethyl Disiloxane, Bis (trimethylsiloxy) Ethylsilane, and Bis(trimethylsiloxy) Methylsilane.

7. The anodized solid titanium non-stick electrosurgical device of claim 5, wherein the silane coating is applied directly to the entire active electrode area of said anodized solid titanium non-stick electrosurgical device.

8. The anodized solid titanium non-stick electrosurgical device of claim 5, comprising titanium metal selected from at least one of pure titanium or titanium based alloy.

9. The anodized solid titanium non-stick electrosurgical device of claim 5, wherein the active electrode area has a ball nose shape.

10. The anodized solid titanium non-stick electrosurgical device of claim 5, wherein the active electrode area has a hook end.

11. The anodized solid titanium non-stick electrosurgical device of claim 5, wherein the active electrode area is a needle.

12. The anodized solid titanium non-stick electrosurgical device of claim 5, wherein the active electrode area is a pair of blades.

13. The anodized solid titanium non-stick electrosurgical device of claim 5, wherein, after the silane coating has become scratched or abraded, silane coating has been reapplied in a liquid state over the anodized solid titanium electrosurgical device and repolymerized and re-sterilized for re-use of the anodized solid titanium electrosurgical device.

14. The anodized solid titanium non-stick electrosurgical device of claim 5, wherein the roughened active electrode area has been sand blasted.

15. The anodized solid titanium non-stick electrosurgical device of claim 5, wherein the silane coating comprises a bifunctional silane compound.

16. An electrosurgical device comprising:
    a proximal end adapted to be held, and
    a distal end with an active electrode area, said distal end operably associated with the proximal end and comprised of roughened oxidized solid titanium coated with silane, the distal end adapted to contact body tissue of a subject undergoing an electrosurgical procedure in a non-stick manner as may be determined by a reduction in carbonaceous remains sticking to the active electrode area while the electrosurgical device is used in the electrosurgical procedure.

17. The electrosurgical device of claim 16, wherein the silane has been coated onto the oxidized and roughened solid titanium via an in situ polymerized silane coating so as to apply the silane directly against the oxidized solid titanium.

* * * * *